United States Patent [19]

Nohda

[11] 4,364,646
[45] Dec. 21, 1982

[54] POSITION ADJUSTING DEVICE FOR OPHTHALMOLOGIC INSTRUMENT

[75] Inventor: Masao Nohda, Yokohama, Japan

[73] Assignee: Nippon Kogaku K.K., Tokyo, Japan

[21] Appl. No.: 126,846

[22] Filed: Mar. 3, 1980

[30] Foreign Application Priority Data

Mar. 13, 1979 [JP] Japan .............................. 54-31221[U]

[51] Int. Cl.³ .............................................. A61B 3/10
[52] U.S. Cl. .................................... 351/208; 351/214
[58] Field of Search ........................... 351/13, 16, 6, 14

[56] References Cited

U.S. PATENT DOCUMENTS

| 890,580 | 6/1908 | Sutcliffe . | |
|---|---|---|---|
| 3,864,030 | 2/1975 | Cornsweet | 351/7 |
| 3,871,772 | 3/1975 | Munnerlyn et al. | 351/13 X |
| 4,252,420 | 2/1981 | Kohayakawa | 351/7 |

Primary Examiner—John K. Corbin
Assistant Examiner—Rodney Bovernick
Attorney, Agent, or Firm—Fitzpatrick, Cella, Harper & Scinto

[57] ABSTRACT

A position adjusting device attached to an ophthalmologic measuring instrument to accurately position an eye to be examined with respect to the ophthalmologic measuring instrument comprises projection means for projecting a predetermined projection pattern upon the eye to be examined, an objective lens group for observing therethrough the reflected image of the projection pattern by the cornea of said eye, a field stop provided at the image forming position of the objective lens group, a light-intercepting member provided near the objective lens group and having two openings outside of the optic axis of the objective lens group, a reflecting member obliquely disposed on the optic axis of the objective lens group rearwardly of and near the light-intercepting member, a position adjusting standard chart, and a projection lens for projecting the image of the standard chart onto the position of the field stop through the reflecting member.

10 Claims, 10 Drawing Figures

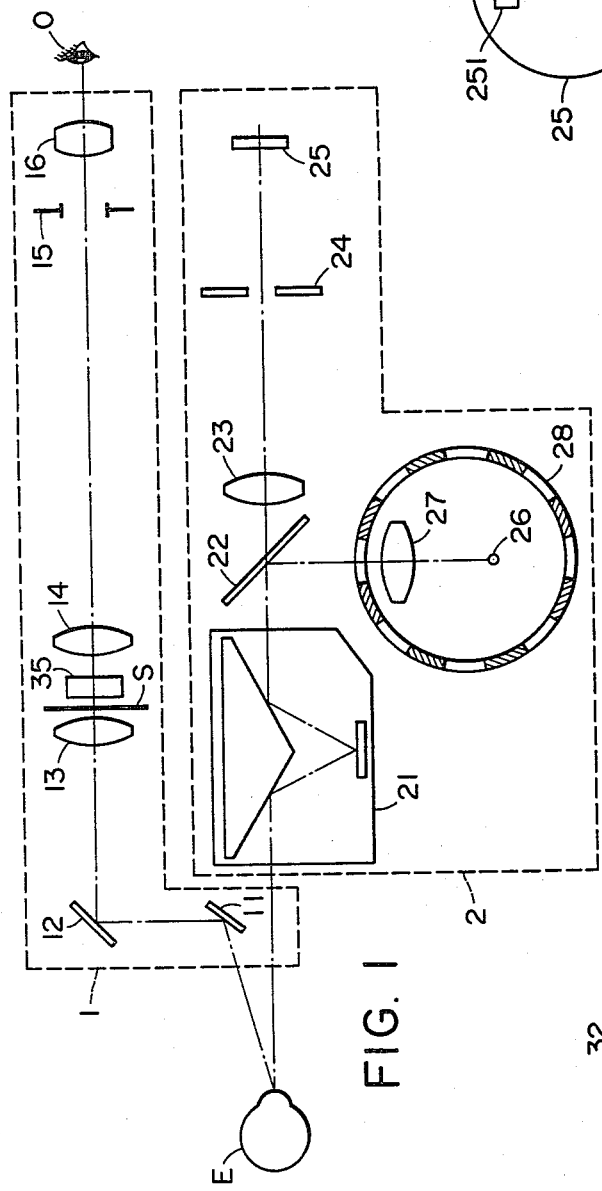
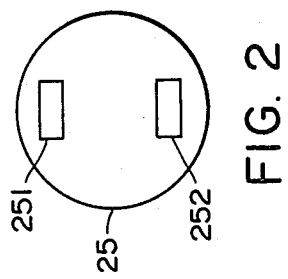
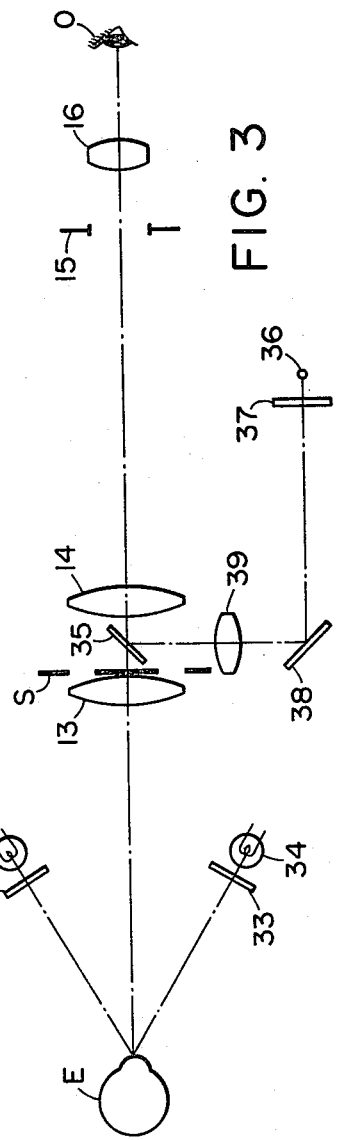

POSITION ADJUSTING DEVICE FOR OPHTHALMOLOGIC INSTRUMENT

BACKGROUND OF THE INVENTION

1. Field of the Invention

This invention relates to a position adjusting device attached to an ophthalmologic measuring instrument to adjust the position of various ophthalmologic measuring instruments with respect to an eye to be examined.

2. Description of the Prior Art

In an ophthalmologic measuring instrument such as a refractometer or an ophthalmometer, it is necessary to accurately adjust the position of the measuring device with respect to an eye to be examined in order to enhance the measurement accuracy and various devices have been proposed for such purpose. As a simple device, there is known one in which a certain pattern is projected upon the eye to be examined and the image of such pattern by the cornea of the eye is observed, but when the environment of the eye to be examined is dark, accurate position adjustment has been difficult to do. There is also known an automatic follow-up device in which the movement of the eye to be examined is photoelectrically detected to cause the measuring device to automatically follow said movement, or a device using infrared rays, but these have been considerably complicated and of large-scale construction and have been disadvantageous for making the entire measuring device compact.

SUMMARY OF THE INVENTION

It is the object of the present invention to provide a simple and compact position adjusting device which can effect accurate position adjustment even when the environment of the eye to be examined is dark.

The invention will become fully apparent from the following detailed description thereof taken in conjunction with the accompanying drawings.

BRIEF DESCRIPTION OF THE DRAWINGS

FIG. 1 is a schematic side view of an embodiment of the present invention used with an eye refractive power measuring device.

FIG. 2 is a plan view of the light-receiving member in the eye refractive power measuring device.

FIG. 3 is a plan view of the embodiment shown in FIG. 1.

DESCRIPTION OF THE PREFERRED EMBODIMENTS

Figure 4:
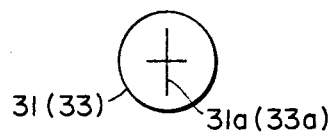
FIG. 4 is a plan view of the green filter in the embodiment of FIG. 3.

The invention will hereinafter be described with respect to an embodiment thereof. FIG. 1 is a side view schematically showing the construction of an embodiment in which the position adjusting device according to the present invention is used with an eye refractive power measuring device. The position adjusting device 1 and the measuring device 2 are provided integrally with each other. This eye refractive power measuring device is based on the so-called skiascopy.

The light beam from a spot light source 26 provided within a rotatable drum 28 having a slit-like opening passes through a projection lens 27 and is reflected by a beam splitter 22, and then passes through an image rotating prism 21 to an eye E to be examined, and by the rotation of the rotatable drum 28, a linear light beam scans the fundus of the eye E. The reflected light from the fundus of the eye E again passes through the image rotating prism 21 to the beam splitter 22, and passes through the beam splitter and is subjected the action of an objective lens 23 and then passes through a diaphragm member 24 to a light-receiving member 25. Two light-receiving elements 251 and 252 are provided on the light-receiving member 25 outside of the center thereof, as shown in the plan view of FIG. 2, and the movement of the reflected light from the fundus of the eye is measured by these light-receiving elements.

Figure 5:
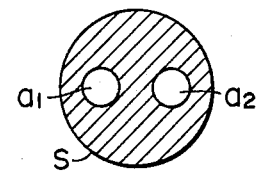
FIG. 5 is a plan view of the light-intercepting stop in the embodiment of FIG. 3.
Figure 6:
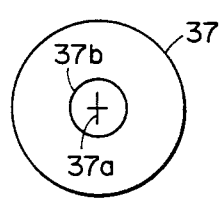
FIG. 6 is a plan view of the chart plate in the embodiment of FIG. 3.

Now, a plan view of the position adjusting device 1 is shown in FIG. 3. In FIG. 3, mirrors 11 and 12 shown in FIG. 1 are omitted for simplicity. Two green filters 31 and 33 both have a light-transmitting portion provided only by a reticle as shown in FIG. 4, and light sources 32 and 34 illuminate these, respectively, so that the green reticles are projected as a projection pattern onto the eye E. A virtual image of this reticle pattern is formed by the cornea of the eye, and this is formed as a real image at the position of a field stop 15 by a first objective lens 13 and a second objective lens 14. Between the first objective lens 13 and the second objective lens 14, there is provided a light-intercepting stop S having two openings $a_1$ and $a_2$ outside of the center thereof, as shown in FIG. 5, and a mirror 35 is obliquely disposed on the optic axis adjacent to the central light-intercepting portion of the light-intercepting stop S. A chart plate 37 illuminated by a light source 36 is provided with light-transmitting portions comprising a cross chart 37a and a small circular chart 37b as position adjusting standard charts, as shown in FIG. 6. The light beam transmitted through the chart plate 37 and reflected by a mirror 38 passes through a projection lens 39 and is reflected by the mirror 35 and passes through the second objective lens 14, whereafter the light beam forms the images of the cross chart 37a and the small circular chart 37b at the position of the field stop 15. The center of the image of this cross chart is exactly coincident with the optic axis of the objective lens 13 and 14. Accordingly, at the position of the field stop 15, in addition to the two images of the reticle patterns 31a and 33a on the green filters 31 and 33, the images of the cross chart 37a and the small circular chart 37b on the chart plate 37 are formed at the center of the view field, and the examiner 0 may observe these through an eyepiece 16.

Figure 7:
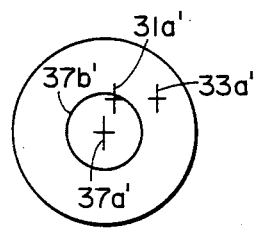
FIG. 7 shows the positional relation between images observed by the examiner during the distance adjustment of the entire device.
Figure 8:
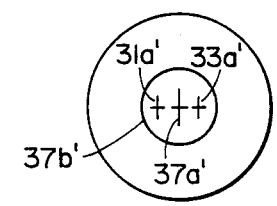
FIG. 8 shows the positional relation between images observed by the examiner at the termination of the position adjustment of the eye to be examined.

The two light beams forming the images of the reticle patterns 31a and 33a are caused to pass through the portion outside of the optic axis by the light-intercepting stop S and therefore, when the entire device is not positioned at a predetermined distance with respect to the eye to be examined, the reticle patterns always become dual images, and distance adjustment is effected by making the dual images coincident with each other, as is well known. When the distance adjustment has been terminated, the positional relation between the images observed by the examiner O is such that, as shown in FIG. 7, for example, the images 31a' and 33a' of the reticle patterns 31a and 33a on the green filters 31 and 33 are offset with respect to the images 37a' and 37b' of the cross chart 37a and the small circular chart 37b as the position adjusting standard charts. The entire device is moved to the left and right and up and down so that the images 31a' and 33a' of the two reticle patterns are positioned symmetrically with respect to the image 37a' of the cross chart, as shown in FIG. 8, whereby the position adjustment of the eye to be examined is completed. In the observation view field, the images 31a' and 33a' of the two reticle patterns are green and the image 37a' of the cross chart and the image 37b' of the small circular chart is white and therefore, it is easy to discriminate between these images and the required discrimination as to whether or not three crosses stand on a straight line and whether or not the spacing between the reticles is bilateral symmetry leads to great simplicity and accuracy of the position adjustment.

In the present embodiment, as shown in FIG. 3, two sets of green filters and illuminating light sources are provided on the opposite sides of the optic axis of the objective lens 13 so that two reticle patterns are projected upon the eye to be examined, whereas the position adjustment is also possible by a single reticle pattern. In this latter case, it is desirable that a new chart to be coincident with this reticle pattern be provided on the chart plate 37.

Figure 9:
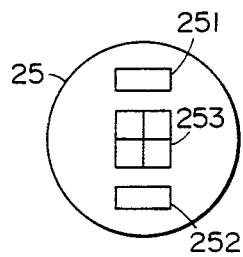
FIG. 9 is a plan view showing another example of the light-receiving member in the eye refractive power measuring device.
Figure 10:
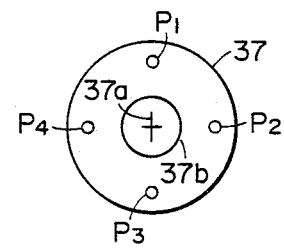
FIG. 10 is a plan view of a chart plate to be used with the light-receiving member of FIG. 9.

Also, as the light-receiving member 25 of the eye refractive power measuring device 2 used in the present embodiment, a four-divided light-receiving element 253 may be provided in the central portion in addition to the two light-receiving elements 251 and 252, as shown in FIG. 9, and the position of the reflected light from the cornea of the eye to be examined may be detected by the four-divided light-receiving element to thereby detect the position of the device. Alternatively, in the above-described embodiment of the present invention, four display elements $P_1$, $P_2$, $P_3$ and $P_4$ such as light-emitting diodes may be provided on the chart plate 37 along the circumference thereof as shown in FIG. 10, so that the outputs of the four-divided light-receiving element may be displayed by these four display elements, whereby for the position adjustment of the examiner, the indication of the direction of movement of the entire device or the display of whether or not it is within an allowable range may be effected and the completion of the position adjustment may be displayed.

Further, in the above-described embodiment, two first and second objective lenses 13 and 14 are used, whereas a single objective lens may of course be used and the light-intercepting stop S and the mirror 35 obliquely disposed adjacent thereto may be provided near the objective lens, whether forwardly or rearwardly thereof. Also, the foregoing embodiment is of such a construction that the examiner observes a spatial image formed at the position of the field stop 15, whereas it is of course possible to make various images easier to observe by providing a screen at the position of the field stop 15. Again in this case, the circumference of the screen performs the function of a substantial field stop.

According to the present invention, as has been described above, there is achieved a compact position adjusting device which is simple in construction and yet enables position adjustment to be effected accurately even when the environment of the eye to be examined is dark.

Of course, the position adjusting device according to the present invention is usable not only with an eye refractive power measuring device but also with various eye measuring instruments such an ophthalmometer or the like.

I claim:

1. A position adjusting device attached to an ophthalmologic measuring instrument to accurately position an eye to be examined with respect to the ophthalmologic measuring instrument, said device comprising:
   (a) first projection means for projecting a predetermined projection pattern upon the eye to be examined;
   (b) an objective lens group for forming therethrough the reflected image of said projection pattern by the cornea of said eye to be examined;
   (c) a field stop provided at the image forming position of said objective lens group;
   (d) a light-intercepting member provided near said objective lens group and having two openings outside of the optic axis of said objective lens group;
   (e) a reflecting member obliquely disposed on the optic axis of said objective lens group rearwardly of and near said light-intercepting member;
   (f) second projection means for projecting a standard chart image onto the position of said field stop through the reflection on said reflecting member so as to coincide the center of the standard chart image with the optical axis of said objective lens; and
   (g) an eyepiece for observing the image of said projection pattern and the image of said standard chart both formed at the position of said field stop;
   whereby the distance adjustment between said ophthalmologic measuring instrument and said eye to be examined is achieved by moving said measuring instrument relative to said eye so that dual images resulting from light rays passing through said two openings of said light-intercepting member respectively coincide with each other, and whereby the position adjustment of said ophthalmologic measuring instrument and said eye to be examined may be achieved by moving said measuring instrument relative to said eye so that the image of said projection pattern and the image of said standard chart are formed in a predetermined positional relation at the position of said field stop.

2. The position adjusting device according to claim 1, wherein said objective lens group includes first and second objective lenses, and said light-intercepting member and said reflecting member are provided between said two objective lenses.

3. The position adjusting device according to claim 2, wherein said ophthalmologic measuring instrument is an eye refractive power measuring device having light supply means for supplying a linear light beam to said eye to be examined and scanning said eye, and a light-receiving member for detecting the reflected light from the fundus of said eye to be examined.

4. The position adjusting device according to claim 1, 2 or 3, wherein said first projection means has two reticule patterns and projects the two reticule patterns upon the eye to be examined.

5. The position adjusting device according to claim 4, wherein said standard chart includes a reticle chart.

6. The position adjusting device according to claim 1, wherein said second projection means includes a projection lens and a chart plate having a standard chart thereon to be projected onto the position of said field stop by said projection lens.

7. The position adjusting device according to claim 5, wherein the image of said standard chart and the image of said projection pattern are of different colors.

8. The position adjusting device attached to an ophthalmologic measuring instrument to accurately position the ophthalmologic measuring instrument with respect to an eye to be examined, said device comprising, first projection means for projecting a predetermined projection pattern upon the eye, an objective lens group for forming therethrough the reflected image of said projection pattern by the cornea of said eye at a predetermined position, and a light-intercepting member provided near said objective lens group and having two openings outside of the optical axis of said objective lens group, the improvement residing in that said device further comprises a reflecting member obliquely disposed on the optical axis of said objective lens group rearwardly of and near said light-intercepting member, and second projection means for projecting the image of a standard chart onto said predetermined position through the reflection on said reflecting member, whereby the distance adjustment between said ophthalmologic measuring instrument and said eye to be examined is achieved by moving said measuring instrument relative to said eye so that dual images resulting from light rays passing through said two openings of said light-intercepting member respectively coincide with each other, and whereby the position adjustment of said ophthalmologic measuring instrument and said eye to be examined may be achieved by moving said measuring instrument relative to said eye so that the image of said projection pattern and the image of said standard chart are formed in a predetermined positional relation at a predetermined position.

9. A position adjusting device according to claim 8, wherein said first projection means includes two reticule patterns each projected onto the cornea of said eye symmetrically with respect to the optical axis of said objective lens group, and said second projection means includes a cross chart as a standard chart projected on said optical axis of said objective lens group, whereby the distance adjustment between said ophthalmologic measuring instrument and said eye to be examined is achieved by moving said measuring instrument relative to said eye so that dual images resulting from light rays passing through said two openings of said light-intercepting member respectively coincide with each other, and whereby the position adjustment of said ophthalmologic measuring instrument and said eye to be examined may be achieved by moving said measuring instrument relative to said eye so that the image of said two reticule patterns and the image of said cross chart stand on a straight line and the spacing between the image of said cross chart and the image of said two reticule patterns are in bilateral symmetry.

10. The position adjusting device according to claim 9, wherein the image of said two reticule patterns has a different color from that of said cross chart as a standard chart.

* * * * *